US010604477B2

United States Patent
Sato et al.

(10) Patent No.: US 10,604,477 B2
(45) Date of Patent: Mar. 31, 2020

(54) UREA MANUFACTURING METHOD AND UREA MANUFACTURING APPARATUS

(71) Applicant: Toyo Engineering Corporation, Tokyo (JP)

(72) Inventors: Keishi Sato, Chiba (JP); Kenji Yoshimoto, Chiba (JP); Haruyuki Morikawa, Chiba (JP)

(73) Assignee: TOYO ENGINEERING CORPORATION, Tokyo (JP)

( * ) Notice: Subject to any disclaimer, the term of this patent is extended or adjusted under 35 U.S.C. 154(b) by 7 days.

(21) Appl. No.: 15/758,295

(22) PCT Filed: Aug. 31, 2016

(86) PCT No.: PCT/JP2016/075505
§ 371 (c)(1),
(2) Date: Mar. 7, 2018

(87) PCT Pub. No.: WO2017/043391
PCT Pub. Date: Mar. 16, 2017

(65) Prior Publication Data
US 2018/0258034 A1 Sep. 13, 2018

(30) Foreign Application Priority Data
Sep. 8, 2015 (JP) .............................. 2015-176433

(51) Int. Cl.
*C07C 273/04* (2006.01)
*C07C 273/16* (2006.01)
(Continued)

(52) U.S. Cl.
CPC ............ *C07C 273/04* (2013.01); *B01D 3/009* (2013.01); *B01D 5/009* (2013.01); *B01D 5/0081* (2013.01);
(Continued)

(58) Field of Classification Search
CPC .................................................... C07C 273/04
See application file for complete search history.

(56) References Cited

U.S. PATENT DOCUMENTS 5,750,780 A * 5/1998 Rescalli ................ C07C 273/04
564/66
6,552,224 B2 * 4/2003 Pagani .................. C07C 273/04
564/66
(Continued)

FOREIGN PATENT DOCUMENTS

EP 0329215 A1 2/1989
JP 56-53644 A 5/1981
(Continued)

OTHER PUBLICATIONS

WIPO, Japanese International Search Authority, International Search Report in English, International Search Report and Written Opinion in Japanese dated Oct. 11, 2016 in International Patent Application No. PCT/JP2016/075505, 10 pages.

*Primary Examiner* — Jennifer A Leung
(74) *Attorney, Agent, or Firm* — Masuvalley & Partners

(57) ABSTRACT

Provided are urea manufacturing method and apparatus, which can increase the conversion ratio into urea and to reduce the consumption of steam. The temperature of the reactor is increased by introducing the entire amount of raw material ammonia and introducing a portion of the decomposed gas from the stripper into the reactor. The raw material ammonia is preferably heated using the steam condensate generated in the purification step, and/or the steam generated by the heat of condensation of the decomposed gas and the unreacted substances in the condensation step. The heating temperature is preferably between 70 and 140° C.

12 Claims, 2 Drawing Sheets

(51) Int. Cl.
*B01J 19/00* (2006.01)
*B01D 3/00* (2006.01)
*B01D 5/00* (2006.01)

(52) U.S. Cl.
CPC ......... *B01J 19/0053* (2013.01); *C07C 273/16* (2013.01)

(56) References Cited

U.S. PATENT DOCUMENTS

| | | | |
|---|---|---|---|
| 2006/0270872 A1* | 11/2006 | Kojima | C07C 273/04 564/67 |
| 2010/0168473 A1* | 7/2010 | Zwart | B01D 3/343 564/67 |

FOREIGN PATENT DOCUMENTS

| JP | 61-109760 A | 5/1986 |
|---|---|---|
| JP | 9-20745 A | 1/1997 |
| JP | 9-20746 A | 1/1997 |
| JP | 10-182587 A | 7/1998 |

* cited by examiner

UREA MANUFACTURING METHOD AND UREA MANUFACTURING APPARATUS

RELATED APPLICATIONS

This application is the U.S. National Phase of and claims priority to International Patent Application No. PCT/JP2016/075505, International Filing Date Aug. 31, 2016, entitled Urea Production Method And Urea Production Device; which claims benefit of Japanese Patent Application No. 2015-176433 filed Sep. 8, 2015; both of which are incorporated herein by reference in their entireties.

TECHNICAL FIELD

The present invention relates to urea manufacturing method and manufacturing apparatus, more specifically to urea manufacturing method and manufacturing apparatus, which can increase the ratio of conversion into urea and consume less steam.

BACKGROUND ART

Urea is manufactured by the following method: first, ammonia ($NH_3$) and carbon dioxide ($CO_2$) are subjected to reaction to produce ammonium carbamate ($NH_2COONH_4$) as represented by Formula (1), and then, ammonium carbamate is subjected to dehydration reaction to produce urea ($NH_2CONH_2$) and water ($H_2O$) as represented by Formula (2).

(1)

(2)

Both reactions are the equilibrium reaction but the reaction of Formula (1) is the exothermic reaction while the reaction of Formula (2) is the endothermic reaction. For this reason, various schemes have been studied to increase the conversion ratio from the raw materials of ammonia and carbon dioxide to urea.

Patent Literature 1 has described the improved urea synthesis method with the characteristics below. In this method, ammonia and carbon dioxide react with each other under the urea synthesis temperature and pressure in the urea synthesis zone. The resulting urea synthesis solution containing urea, unreacted ammonia, unreacted carbon dioxide, and water is brought into contact with at least a portion of the raw material carbon dioxide under heating and under the pressure substantially equal to the urea synthesis pressure in the stripping zone. This causes the unreacted ammonia and the unreacted carbon dioxide to be separated as the mixed gas of ammonia, carbon dioxide, and water. The urea synthesis solution containing the unreacted ammonia and the unreacted carbon dioxide which are not separated is processed further; thus, the urea is obtained. Meanwhile, the mixed gas separated in the stripping zone is introduced to the bottom of the vertical condensation zone and is brought into contact with the absorbing medium while being cooled. This causes the mixed gas to be condensed. The resulting condensate circulates in the urea synthesis zone.

In the third example of Patent Literature 1, ammonia as the raw material is heated up to 175° C. in the heat exchanger and then introduced into the ejector. The ejector plays the role of sending the solution from the condenser to the reactor under the boosted pressure. Carbon dioxide ($CO_2$) is introduced into the reactor and the stripper. The temperature of the solution in the condenser is adjusted to 185° C. The solution goes through the ejector to be introduced into the reactor. In the reactor, urea is synthesized through the dehydration reaction of the ammonium carbamate. This reaction is endothermic reaction. By increasing the temperature of the raw material ammonia up to 175° C., the temperature of the reactor is maintained so as not to decrease below 185° C.

According to Patent Literature 2, the temperature of the reaction zone where the urea synthesis is carried out is increased by introducing at least a portion of a gas mixture discharged from the stripping zone into the reaction zone and condensing the introduced gas mixture.

CITATION LIST

Patent Literatures

PATENT LITERATURE 1: JP-A-H-10-182587
PATENT LITERATURE 2: EP 0329215 A, Specification
PATENT LITERATURE 3: JP-A-61-109760

SUMMARY OF THE INVENTION

Problems to be Solved by the Invention

As the reactor has the higher temperature, the conversion ratio of ammonium carbamate into urea is increased and the unreacted substances are therefore decreased. Ammonium carbamate is decomposed by the heating with steam. Therefore, as the ammonium carbamate is decreased, less steam is required to separate the unreacted substances. In addition, as the temperature of the reactor is higher, the heat to enter the stripper is increased. Increasing the temperature of the reactor is therefore effective to reduce the steam to be consumed in the stripper.

The third example of Patent Literature 1 has examined the method of increasing the temperature of the raw material ammonia in order to increase the temperature of the reactor. The temperature of the raw material ammonia, however, has risen to 175° C. To increase the temperature further, heating with the high-pressure steam is considered but in this case, more steam is consumed.

In another method, the temperature of the reactor is increased by introducing a portion of carbon dioxide into the reactor but in this case, the amount of carbon dioxide to enter the stripper is reduced. The reduction of carbon dioxide makes it difficult to decompose and separate the unreacted substances in the stripper. Therefore, more unreacted substances remain in the urea synthesis solution exit from the bottom of the stripper. The unreacted substances are separated in the downstream urea purification step. The separated unreacted substances are recovered by decomposing and absorbing in the purification step. In order to recover the substances, however, water is required as the absorbent solvent. Using the water here will result in more recovered solution, and more water returns to the reactor as the recovered solution. The presence of water reduces the conversion ratio into urea, which is determined by the synthesis equilibrium. For these reasons, the amount of water returned to the reactor is preferably as small as possible. In this sense, the urea synthesis solution from the bottom of the stripper preferably contains as little ammonium carbamate as possible. Into the stripper, as large amount of carbon dioxide as possible is preferably introduced. If the amount of carbon dioxide introduced into the stripper is reduced, the conversion ratio into urea is decreased and the unreacted substances will increase. Thus, more steam is consumed in the manufacture of urea. Moreover, less gas is generated by the decomposition and separation of the unreacted substances in the stripper. This reduces the heat of condensation in the condenser. Accordingly, less steam is generated from the heat of condensation. That is to say, it has been impossible to increase the temperature of the reactor without suppressing the decrease in carbon dioxide introduced into the stripper as much as possible or without continuing to heat until the temperature of ammonia becomes high.

It is an object of the present invention to provide urea manufacturing method and apparatus, which can increase the conversion ratio into urea and consume less steam.

Solution to the Problems

A urea manufacturing method of the present invention includes: an ammonia introduction step of introducing an entire amount of raw material ammonia into a reactor; a synthesis step of reacting carbon dioxide and ammonia reaction under a condition of excessive ammonia in the reactor, thereby providing a synthesis mixture containing urea, ammonium carbamate, water, unreacted ammonia, and unreacted carbon dioxide; a decomposition step of decomposing the ammonium carbamate by heating the synthesis mixture and stripping using at least a portion of raw material carbon dioxide as an auxiliary agent, thereby providing a decomposed gas containing ammonia and carbon dioxide, and a urea synthesis solution containing ammonia, carbon dioxide, water, and urea; a purification step of separating an unreacted substances including ammonia, carbon dioxide, and water from the urea synthesis solution, thereby providing a purified urea solution and recovering the separated unreacted substances; a decomposed gas introduction step of introducing a portion of the decomposed gas into the reactor; a condensation step of condensing the rest of the decomposed gas and at least a portion of the unreacted substances recovered in the purification step in the condenser, thereby providing a condensate; and a condensate introduction step of introducing the obtained condensate to the reactor using an ejector which uses at least a portion of the raw material ammonia as a driving fluid.

A urea manufacturing apparatus of the present invention includes: a reactor in which carbon dioxide and ammonia are reacted under a condition of excessive ammonia, thereby providing a synthesis mixture containing urea, ammonium carbamate, water, unreacted ammonia, and unreacted carbon dioxide; an ammonia introduction line that is used to introduce an entire amount of raw material ammonia into the reactor; a stripper that decomposes the ammonium carbamate by heating the synthesis mixture and stripping using at least a portion of raw material carbon dioxide as an auxiliary agent, thereby providing a decomposed gas containing ammonia and carbon dioxide, and a urea synthesis solution containing ammonia, carbon dioxide, water, and urea; a purification system that purifies urea by separating the unreacted substances including ammonia, carbon dioxide, and water from the urea synthesis solution, and recovers the separated unreacted substances; a decomposed gas introduction line that is used to introduce a portion of the decomposed gas into the reactor; a condenser that condenses the rest of the decomposed gas and at least a portion of the unreacted substances recovered in the purification system in the condenser, thereby providing a condensate; and a condensate introduction line that is used to introduce the obtained condensate to the reactor using an ejector which uses at least a portion of the raw material ammonia as a driving fluid.

Effects of the Invention

According to the present invention, the urea manufacturing method and apparatus, which can increase the conversion ratio into urea and consume less steam, can be provided.

DESCRIPTION OF THE EMBODIMENTS

Figure 1:
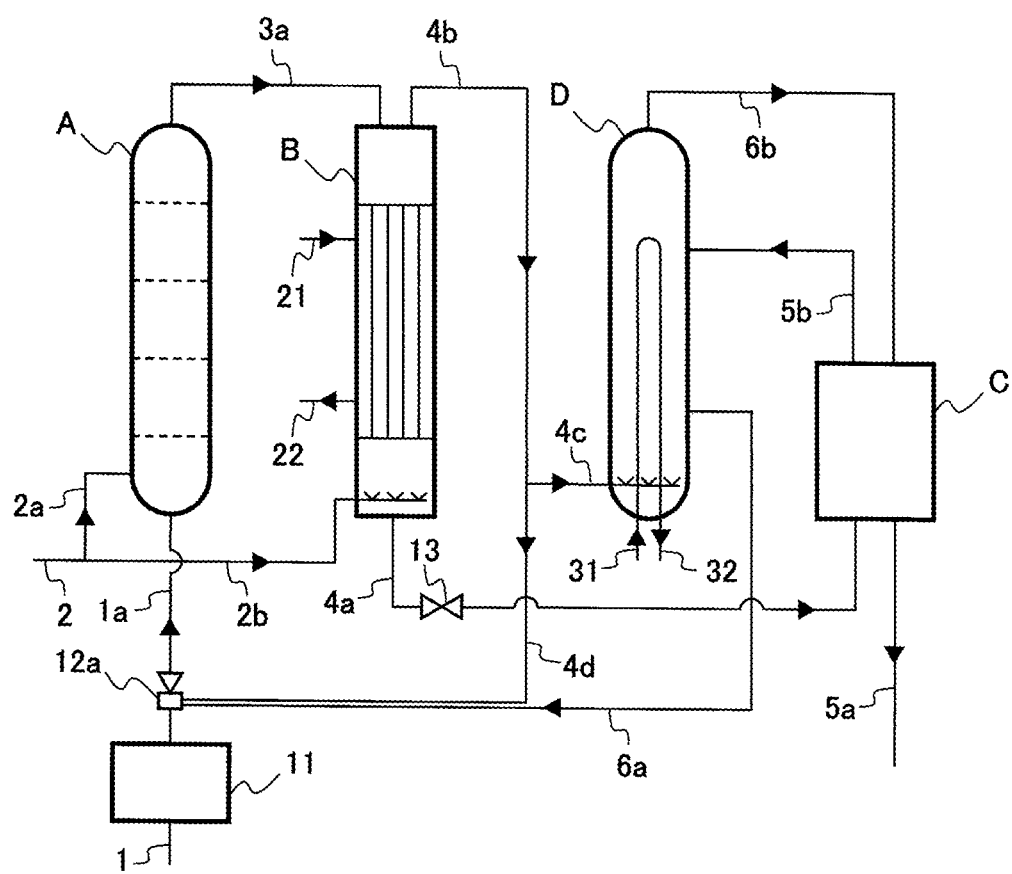
FIG. 1 is a diagram illustrating a configuration example of a urea manufacturing apparatus according to the present invention.

FIG. 1 illustrates a configuration example of a urea manufacturing apparatus according to the present invention. The apparatus illustrated in FIG. 1 includes a reactor A, a stripper B, a purification system C, and a condenser D.

In the reactor A, ammonia ($NH_3$) and carbon dioxide ($CO_2$) are subjected to reaction to produce ammonium carbamate, and further ammonium carbamate is subjected to dehydrogenation reaction to produce urea and water (urea synthesis step). In the urea synthesis step, ammonia is excessive in consideration of the equilibrium pressure of the synthesis mixture to be obtained. In the urea synthesis step, the molar ratio of the $NH_3$ component to the $CO_2$ component (N/C) is preferably between 3.0 and 4.0, more preferably between 3.5 and 4.0 (3.7 for example).

The $NH_3$ component contains, in addition to the actually present ammonia, ammonia converted into ammonium carbamate and ammonia converted into urea. Therefore, the molar amount of the $NH_3$ component corresponds to the total value of twice as much as the molar amount of urea, twice as much as the molar amount of ammonium carbamate, and the molar amount of ammonia. The $CO_2$ component contains, in addition to the actually present carbon dioxide, carbon dioxide converted into ammonium carbamate and carbon dioxide converted into urea. Therefore, the molar amount of the $CO_2$ component corresponds to the total value of the molar amount of urea, the molar amount of ammonium carbamate, and the molar amount of carbon dioxide.

The two stage reactions of the urea synthesis step are both the equilibrium reaction. Therefore, in the urea synthesis step, the synthesis mixture containing urea (including a small amount of biuret), ammonium carbamate, water, unreacted ammonia, and unreacted carbon dioxide is obtained. The ammonium carbamate contained in the synthesis mixture is decomposed in the next decomposition step, and the unreacted raw materials need to be separated. Therefore, it is more preferable that the conversion rate to urea in the reactor A be higher. The reactor A is accordingly operated at the high temperature (from 175 to 200° C.) and high pressure (from 130 to 200 bar).

Ammonia as the raw material is introduced into the reactor A through an ammonia introduction line 1 (ammonia introduction step). Carbon dioxide as the raw material is introduced into the reactor A through carbon dioxide introduction lines 2 and 2a. Carbon dioxide to be introduced here is usually approximately 10 wt % of the necessary amount as the raw material. Some carbon dioxide and ammonia are also supplied from the condenser D, which will be described below, through a condensate introduction line 6a and a raw material introduction line 1a. In addition, other portions of carbon dioxide and ammonia are also supplied through decomposed gas lines 4b and 4d and the raw material introduction line 1a as a portion of a decomposed gas separated in the stripper B to be described below. The condensate introduction line 6a and the decomposed gas line 4d are connected to an ejector 12a. The ejector 12a uses as a driving fluid, at least a portion of the raw material ammonia introduced through the ammonia introduction line 1.

In the present invention, the entire amount of raw material ammonia is introduced into the reactor A through the ammonia introduction line 1. This can achieve higher N/C, which results in the larger conversion ratio of $CO_2$ into urea. Accordingly, less steam is consumed to separate the decomposed gas in the stripper B.

In the present invention, using the ejector 12a lower the ammonia introduction line 1 and the condenser D elevation, and also makes the operation more stable. If the entire amount of raw material ammonia is introduced into the reactor A without using the ejector 12a, it is necessary to send the condensate into the reactor A under gravity. In this case, the condenser D needs to be located above the top of the reactor A by at least 5 m, preferably 10 m. In this case, the operation fluctuation affects the pressure balance between the reactor A and the condenser D. This may affect the introduction of the condensate into the reactor A and result in the instable operation but the present invention will solve such a problem.

In the present invention, preferably, the raw material ammonia before being introduced into the reactor A is heated in an ammonia pre-heater 11. This can increase the temperature in the reactor A and therefore increase the conversion ratio of $CO_2$ into urea. Accordingly, less steam is consumed to separate the decomposed gas in the stripper B. To heat the raw material ammonia, preferably, the steam condensate generated in the purification step (steam condensate generated by condensing the steam used in the heating in the purification step and/or the subsequent concentration step of heating and concentrating the purified aqueous urea solution) and/or the steam (LP steam) generated by the heat of condensation in the condensation step.

The raw material ammonia is preferably heated up to from 70 to 140° C. More specifically, the raw material ammonia is heated up to approximately from 70 to 90° C. by the steam condensate, and heated further by the LP steam up to approximately from 120 to 140° C. as necessary.

The synthesis mixture obtained in the reactor A is introduced into the stripper B through a synthesis mixture line 3a. In the stripper B, the synthesis mixture is heated so that ammonium carbamate is decomposed into ammonia and carbon dioxide, and further stripped using at least a portion of raw material carbon dioxide as an auxiliary agent. Thus, the decomposed gas containing ammonia and carbon dioxide is separated (decomposition step). However, the ammonia and carbon dioxide cannot be fully separated from urea and water in the synthesis mixture in the stripper B; therefore, the urea synthesis solution containing ammonia, carbon dioxide, water and urea is obtained. Carbon dioxide is contained in the urea synthesis solution as the ammonium carbamate generated from the reaction with ammonia, and the urea synthesis solution from the stripper B usually contains ammonia, including the ammonia as ammonium carbamate, by approximately from 10 to 15 wt %.

Carbon dioxide as the auxiliary agent in the stripping is introduced into the stripper B through carbon dioxide introduction lines 2 and 2b. The stripper B is heated by a heating medium introduced through a stripper heating medium introduction line 21. The heating medium is discharged through a stripper heating medium discharge line 22. The heating medium is usually steam (water vapor). The pressure of the steam is set to, for example, 20 bar.

The urea synthesis solution obtained in the stripper B is discharged through a urea synthesis solution line 4a connected to the bottom of the stripper B. The pressure is reduced using a control valve 13 and the discharged urea synthesis solution becomes a gas-liquid mixture (pressure reduction step). With the control valve 13, usually the pressure is reduced to between 15 and 20 bar (for example, 17 bar), and thus the gas-liquid mixture with a temperature of between 130 and 140° C. is obtained. The concentration of each of ammonia and carbon dioxide contained in the gas-liquid mixture is preferably between 10 and 15 wt %. An apparatus for heating the obtained gas-liquid mixture may be provided.

The gas-liquid mixture is introduced into the purification system C. In the purification system C, the unreacted substances including ammonia, carbon dioxide, and water is separated from the gas-liquid mixture. This provides the purified urea solution and moreover the separated unreacted substances are recovered (purification step).

In the purification system C, the gas-liquid mixture is placed under the pressure suitable to separate the unreacted substances including ammonia, carbon dioxide, and water. By heating with the steam, moreover, the substantial aqueous urea solution is obtained. In general, when the total amount of ammonia and carbon dioxide remaining in the gas-liquid mixture is approximately 15 wt % or more, for example, the two-stage system as disclosed in Patent Literature 3 is used. This system includes the medium-pressure decomposition column of between 15 and 20 bar (for example, 17 bar), and the low-pressure decomposition column of between 2 and 5 bar (for example, 2.5 bar). If the total amount of residual ammonia and carbon dioxide is less than 15 wt %, the system including only the low-pressure decomposition column is used.

In the purification system C, ammonia and carbon dioxide remaining in the gas-liquid mixture are removed. The heat required for that removal can be obtained from the LP steam generated in the condenser D as described below. The pressure of the LP steam is decided by the operation temperature of the condenser D. As the operation pressure in the synthesis zone is higher, the temperature of the condenser D is higher and the pressure of the LP steam to be generated is also higher. The pressure of LP steam is generally between 4 and 6 bar (between 151 and 164° C.). In the purification system C, such LP steam is used for the heating, but the temperature that can be attained by the medium-pressure decomposition column and the low-pressure decomposition column (especially, the medium-pressure decomposition column) is limited. If the saturated temperature of the steam and the process temperature are different by 10° C., the temperature of the medium-pressure decomposition column heater can be increased up to 141° C. in the case of the LP steam of 5 bar and up to 154° C. in the case of the LP steam of 6 bar. The temperature can be increased further but in this case, the heat transfer area of the heater is increased and from the economical point of view, the further temperature increase is not adopted. If the temperature of the medium-pressure decomposition column is increased, ammonium carbamate and ammonia as the unreacted residue contained in the aqueous urea solution from the medium-pressure decomposition column are decreased and the duty on the low-pressure decomposition column on the downstream side is reduced.

The aqueous urea solution obtained in the purification system C contains a small amount of ammonia and carbon dioxide. The aqueous urea solution may be sent to a urea concentration step through an aqueous urea solution line 5a. In the urea concentration step, the aqueous urea solution may be concentrated by heating in vacuum condition. The urea resulting from the concentration is sent to a production step, where the solid urea is manufactured as a final product.

Ammonia and carbon dioxide separated in the medium-pressure decomposition column and the low-pressure decomposition column are recovered by water as the absorbent solvent in absorbers for each pressure level. The recovered solution obtained in the low-pressure absorber has the absorbing capability under the higher pressure condition, so that this recovered solution is sent to the medium-pressure absorber for condensing gas from the medium-pressure decomposition column and used as the absorbent solvent. The recovered solution obtained in the medium-pressure absorber, which absorbed separated ammonia and carbon dioxide therein is pressurized up to the necessary pressure and then sent to the condenser D. The less water in the recovered solution obtained in medium-pressure absorber contributes to higher conversion ratio into urea in the synthesis step. Thus, the smaller amount of water sent to the low-pressure absorber is therefore preferable. The water to be sent to the low-pressure absorber can be reduced by reducing the unreacted substances separated in the low-pressure decomposition column. To reduce the unreacted substances in the low-pressure decomposition column, preferably, a larger amount of unreacted substances to be separated in the medium-pressure decomposition column, and this can be achieved by increasing the temperature in the medium-pressure decomposition column. For synthesizing urea, it is preferable to remove as many unreacted substances as possible by increasing the temperature of the medium-pressure decomposition column. The method of heating the medium-pressure decomposition column without using the steam generated in the urea synthesis step may be adopted.

The unreacted substances (recovered solution) recovered in the purification system C are introduced into the condenser D through a recovered unreacted substance line 5b. Some of the decomposed gas separated in the stripper B (preferably from 80 to 95 wt %) is introduced into the condenser D through decomposed gas lines 4b and 4c. In the condenser D, the unreacted substances and the decomposed gas are cooled by the cooling medium and condensed. Thus, the condensate is obtained (condensation step). The N/C of the condensate obtained in the condenser D is preferably between 2.5 and 3.5, more preferably between 2.8 and 3.2.

Ammonia and carbon dioxide introduced into the condenser D react with each other to produce ammonium carbamate, and a portion of ammonium carbamate is turned into urea through the dehydration reaction. Thus, the resulting condensate is preferably retained in the condenser D for a certain length of time. Since the condensate can be retained in the condenser D for a sufficient period of time (25 minutes, for example), the bubble column type vertical condensation reactor (also called condenser) is preferably used. The vertical type condensation reactor is preferably the one disclosed in Patent Literature 1, for example.

The cooling medium of the condenser D may be, for example, water. By supplying water to a condenser cooling medium introduction line 31, the LP steam (from 4 to 6 bar) is discharged through a condenser cooling medium discharge line 32. As described above, the LP steam is usually used to heat the medium-pressure decomposition column and the low-pressure decomposition column. But in the present invention, the LP steam is preferably used to heat the raw material ammonia in the ammonia pre-heater 11.

The condensate obtained in the condenser D still contains much unreacted raw material. Thus, the condensate is introduced into the reactor A through a condensate introduction line 6a and the raw material introduction line 1a (condensate introduction step). The condensate is introduced using the ejector 12a, and the ejector 12a uses at least a portion of the raw material ammonia as a driving fluid. The off gas generated from the condenser D (uncondensed gas, mainly including ammonia, carbon dioxide, and inert gas) is returned to the purification system C through an off gas line 6b.

Meanwhile, a portion of the decomposed gas separated in the stripper B is introduced into the reactor A through the decomposed gas lines 4b and 4d and the raw material introduction line 1a (decomposed gas introduction step). By introducing a portion of the decomposed gas directly into the reactor A, the reactor A can be heated.

Here, it is preferable that between 5 and 20 wt % of the decomposed gas be introduced into the reactor A. If 20 wt % or less of the decomposed gas is introduced into the reactor A, the effect of increasing the temperature of the reactor A by the condensation of the decomposed gas is increased. If 5 wt % or more of the decomposed gas is introduced into the reactor A, the temperature of the reactor A is increased effectively. Moreover, the conversion ratio into urea is increased, and the consumption of steam can be reduced efficiently.

Figure 2:
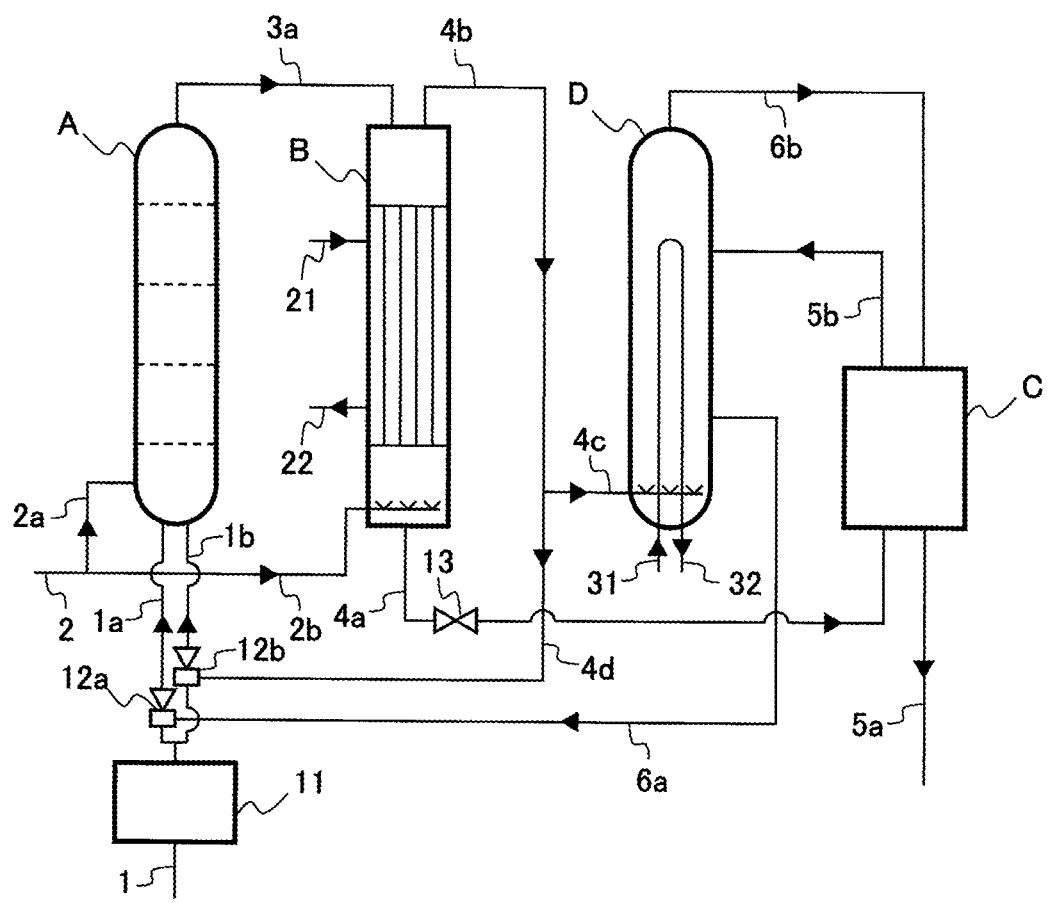
FIG. 2 is a diagram illustrating another configuration example of a urea manufacturing apparatus according to the present invention.

In the apparatus illustrated in FIG. 1, the condensate introduction line 6a and the decomposed gas line 4d are connected to the same ejector 12a, i.e., the condensate and the decomposed gas are introduced into the reactor A through the same raw material introduction line 1a. However, how the condensate and the decomposed gas are introduced is not limited to the aforementioned procedure. The condensate introduction line 6a and the decomposed gas line 4d may alternatively be connected to the different ejectors 12a and 12b as illustrated in FIG. 2. The condensate and the decomposed gas may be introduced into the reactor A through the different raw material introduction lines 1a and 1b. Here, preferably, the ejector 12b uses at least a portion of the raw material ammonia as a driving fluid. The introduction of the decomposed gas from the decomposed gas line 4d to the reactor A is not necessarily by the ejector 12b.

According to the present invention as described above, the temperature of the reactor A can be increased while the decrease in amount of carbon dioxide to be introduced into the stripper B is suppressed as much as possible and without heating the raw material ammonia too high. As a result, according to the present invention, it is possible to increase the conversion ratio into urea and to reduce the consumption of the steam.

EXAMPLES

Example 1

Urea is synthesized using the apparatus illustrated in FIG. 1. The pressure of the synthesis zone (reactor A and stripper B) is set to 160 bar. The condition is set so that the molar ratio (N/C) of the $NH_3$ component to the $CO_2$ component in the reactor A is 3.7. In addition, the condition is set so that the molar ratio of the $H_2O$ component to the $CO_2$ component in the reactor A is 0.58. The $H_2O$ component is calculated by excluding the amount of water generated by the urea synthesis from the amount of water existing actually. That is to say, the molar amount of the $H_2O$ component is obtained by subtracting the molar amount of urea from the molar amount of water.

To the reactor A, 10 wt % of carbon dioxide necessary as the raw material is introduced. In addition, the entire amount of raw material ammonia is heated up to 140° C. and introduced into the reactor A. Thus, the operation temperature of the reactor A is maintained at 182° C. The reaction is caused at this temperature. The synthesis mixture obtained in this reactor A is sent to the stripper B. In the stripper, stripping is performed using rest of raw material carbon dioxide as an auxiliary agent while heating is carried out with the steam of 20 bar, so that the urea synthesis solution and the decomposed gas are separated. The steam is consumed by 0.66 tons per ton of urea in the stripper B.

To the shell side of the vertical submerge type condenser D, 90 wt % of the decomposed gas from the stripper B is sent. The sent decomposed gas is condensed in the presence of the recovered solution from the purification system C, and thus the condensate is obtained. The heat of condensation is removed by generating the steam from the condensate supplied to the tube. The generated steam is used as the steam for heating, which was necessary in the purification step and the subsequent urea concentration step. The condensate generated in the condenser D is returned to the reactor A using the ejector 12a, which uses the raw material ammonia heated up to 140° C. as the driving fluid.

The rest of the decomposed gas from the stripper B (10 wt %) is sent to the reactor A together with the condensate by the ejector 12a. Here, the temperature of the reactor A is increased by 4° C. This increases the conversion ratio of carbon dioxide into urea by 1%. The consumption of steam (20 bar) in the stripper B is reduced by 0.045 tons (approximately 7 wt %) per ton of urea.

Example 2

The urea is synthesized under the same condition as that of Example 1 except that 80 wt % of the decomposed gas from the stripper B is sent to the condenser D and the rest 20 wt % is sent to the reactor A together with the condensate by the ejector 12a. Here, the temperature of the reactor A is increased by 4° C. In addition, when the operation pressure is increased up to 165 bar, the temperature of the reactor A is increased by 8° C., in which case the conversion ratio of carbon dioxide into urea increases by 2% and the consumption of steam (20 bar) in the stripper B is reduced by 0.1 tons (approximately 15 wt %) per ton of urea.

DESCRIPTION OF NUMERALS

A Reactor
B Stripper
C Purification system
D Condenser
1 Ammonia introduction line
1a Raw material introduction line
1b Raw material introduction line
2 Carbon dioxide introduction line
2a Carbon dioxide introduction line
2b Carbon dioxide introduction line
3a Synthesis mixture line
4a Urea synthesis solution line
4b Decomposed gas line
4c Decomposed gas line
4d Decomposed gas line
5a Aqueous urea solution line
5b Recovered unreacted substance line
6a Condensate introduction line
6b Off gas line
11 Ammonia pre-heater
12a Ejector
12b Ejector
13 Control valve
21 Stripper heating medium introduction line
22 Stripper heating medium discharge line
31 Condenser cooling medium introduction line
32 Condenser cooling medium discharge line

The invention claimed is:

1. A urea manufacturing method comprising:
an ammonia introduction step of introducing an entire amount of raw material ammonia directly into a reactor;
a synthesis step of reacting carbon dioxide and ammonia under a condition of excessive ammonia in the reactor, thereby providing a synthesis mixture containing urea, ammonium carbamate, water, unreacted ammonia, and unreacted carbon dioxide;
a decomposition step of decomposing the ammonium carbamate by heating the synthesis mixture and stripping using at least a portion of raw material carbon dioxide as an auxiliary agent in a stripper, thereby providing a decomposed gas containing ammonia and carbon dioxide, and a urea synthesis solution containing ammonia, carbon dioxide, water, and urea;
a purification step of separating water and unreacted substances including ammonia and carbon dioxide from the urea synthesis solution in a purification system, thereby providing a purified urea solution and recovering the separated water and unreacted substances;
a decomposed gas introduction step of introducing a portion of the decomposed gas provided in the stripper directly into the reactor via an ejector which uses the entire amount of the raw material ammonia as a driving fluid;
a condensation step of condensing the rest of the decomposed gas with at least a portion of the water and unreacted substances recovered in the purification step in a condenser, thereby providing a condensate and uncondensed gas, separately;
an off gas returning step for returning the uncondensed gas obtained in the condenser to the purification system; and
a condensate introduction step of introducing the condensate to the reactor using the ejector for introducing the condensate to the reactor.

2. The method according to claim 1, wherein the raw material ammonia is heated in the ammonia introduction step using a steam condensate generated in the purification step and/or a steam generated by heat of condensation in the condensation step.

3. The method according to claim 1, wherein the raw material ammonia is heated up to from 70 to 140° C. in the ammonia introduction step.

4. The method according to claim 1, wherein between 5 and 20 wt % of the decomposed gas is introduced into the reactor in the decomposed gas introduction step.

5. The method according to claim 1, wherein the condenser is a shell and tube condenser, and wherein the decomposed gas from the stripper and the unreacted substances from the purification system are introduced to the shell side of the condenser.

6. The method according to claim 5, wherein the condenser is a bubble column vertical condensation reactor.

7. The method according to claim 1, further comprising:
a carbon dioxide introduction step of introducing a part of raw material carbon dioxide directly into the reactor and the rest of the raw material carbon dioxide directly into the stripper, using a carbon dioxide introduction line that is directly connected to the reactor and the stripper.

8. A urea manufacturing apparatus comprising:
a reactor in which carbon dioxide and ammonia are reacted under a condition of excessive ammonia, thereby providing a synthesis mixture containing urea, ammonium carbamate, water, unreacted ammonia, and unreacted carbon dioxide;
an ammonia introduction line that is used to introduce an entire amount of raw material ammonia directly into the reactor;
a stripper that decomposes the ammonium carbamate by heating the synthesis mixture and stripping using at least a portion of raw material carbon dioxide as an auxiliary agent, thereby providing a decomposed gas containing ammonia and carbon dioxide, and a urea synthesis solution containing ammonia, carbon dioxide, water, and urea;
a purification system that purifies urea by separating water and the unreacted substances including ammonia and carbon dioxide from the urea synthesis solution, and recovers the separated water and unreacted substances;
a decomposed gas introduction line that is used to introduce a portion of the decomposed gas provided in the stripper directly into the reactor, wherein the decomposed gas introduction line is connected to an ejector and the decomposed gas is introduced to the reactor via the ejector, which uses the entire amount of the raw material ammonia as a driving fluid;
a condenser that condenses the rest of the decomposed gas with at least a portion of the water and unreacted substances recovered in the purification system, thereby providing a condensate and uncondensed gas, separately;
an off gas line for returning the uncondensed gas obtained in the condenser to the purification system; and
a condensate introduction line that is used to introduce the condensate to the reactor using the ejector for introducing the condensate to the reactor.

9. The apparatus according to claim 8, wherein the raw material ammonia can be heated in the ammonia introduction line using a steam condensate generated in the purification and/or steam generated in the condenser.

10. The apparatus according to claim 8, wherein the condenser is a shell and tube condenser, and wherein the decomposed gas from the stripper and the unreacted substances from the purification system are introduced to the shell side of the condenser.

11. The apparatus according to claim 10, wherein the condenser is a bubble column vertical condensation reactor.

12. The apparatus according to claim 8, further comprising:
a carbon dioxide introduction line that is directly connected to the reactor and the stripper and that is used to introduce a part of raw material carbon dioxide directly into the reactor and the rest of the raw material carbon dioxide directly into the stripper.

* * * * *